United States Patent [19]
Seketa

[11] Patent Number: 5,442,816
[45] Date of Patent: Aug. 22, 1995

[54] SURGICAL GLOVE

[76] Inventor: Nicholas F. Seketa, 21 Beethoven St., Binghamton, N.Y. 13905

[21] Appl. No.: 14,252

[22] Filed: Feb. 5, 1993

[51] Int. Cl.⁶ .............................................. A41D 19/00
[52] U.S. Cl. .................................... 2/161.7; 2/168
[58] Field of Search ........................ 2/161.8, 161.7, 159, 2/161.6, 161.7, 167–168, 163, 16, 161.1, 162

[56] References Cited

U.S. PATENT DOCUMENTS

| | | | |
|---|---|---|---|
| 730,640 | 2/1903 | Torrens | 2/161.8 |
| 919,406 | 4/1909 | Warren | 2/168 |
| 2,025,357 | 12/1935 | Pagan | 2/161.6 |
| 2,083,935 | 6/1937 | Arnold | 2/161.6 |
| 2,847,676 | 8/1958 | Scott . | |
| 2,949,610 | 8/1960 | Lutsky . | |
| 3,866,245 | 2/1975 | Southerland . | |
| 4,084,265 | 4/1978 | Anfelt . | |
| 4,742,578 | 5/1988 | Seid . | |
| 4,771,482 | 9/1988 | Shlenker | 2/161.7 |
| 4,864,661 | 9/1989 | Gimbel . | |
| 4,924,530 | 5/1990 | Tagaya | 2/168 |
| 4,942,626 | 7/1990 | Stern et al. . | |
| 4,995,119 | 2/1991 | Codkind | 2/161.7 |
| 5,014,361 | 5/1991 | Gray . | |
| 5,070,543 | 12/1991 | Beck . | |
| 5,187,815 | 2/1993 | Stern et al. | 2/161.7 |
| 5,370,900 | 12/1994 | Chen | 2/168 |

FOREIGN PATENT DOCUMENTS 796667 4/1936 France ...................................... 2/163

Primary Examiner—Clifford D. Crowder
Assistant Examiner—Amy B. Vanatta
Attorney, Agent, or Firm—James Creighton Wray

[57] ABSTRACT

The present invention relates to surgical glove designs and materials utilized to resist penetration by sharp needles and instruments as well as being impervious to body fluid and infectious disease causative organisms. An additional feature of the materials utilized is that the tear strength of the glove is substantially increased. The glove is formed of segments which increase in thickness in a direction extending from the distal phalangeal segments to the forearm, and the glove is provided with flex points at the joints. This invention provides a highly protective surgical glove which has universal applications to other medical, industrial, and service occupations.

12 Claims, 2 Drawing Sheets

SURGICAL GLOVE

BACKGROUND OF THE INVENTION

Anfelt in 1976 introduced a process of causing indentations on the outer surface of a glove and protrusions on the inside surface of the glove which facilitated the introduction of operator's hands into surgical gloves. Seid in 1985 proposed utilizing a material composed of a sandwich of latex and tightly interwoven nylon fabric which was present on the palmar surface of the hand which was placed between two layers of latex. The material was hermetically sealed. Gimbel in 1988 improved upon the design by utilizing puncture resistant stalls placed at selected locations on the fingers of the glove. The weave included strands having a weave selected from the class consisting of biaxial, triaxial weave, knit, muliaxial multilayer warp knit, three dimensional cylindrical construction, three dimensional brading, three dimensional ortogonal, and angle interlock construction. In his design of materials a puncture resistant fabric is woven from fiberglas (S-2 Owens Corning), Kevlar strand (DuPont), Kevlar solid, Boron Carbide with a Kevlar backing, balistic nylon, polyethylene (BG Cryovac), Gimbel also can utilize silicon carbide ceramic, a single crystal of aluminum oxide, or a thin coating of aluminum, steel, silver, or other metals, polymers, composites other puncture resistant materials. Polymer materials particularly ethylene copolymer materials are preferred.

SUMMARY OF THE INVENTION

The principle objective of this invention is to provide a family of disposable gloves to include sterilized surgical gloves as well as examination and general purpose gloves which do not require sterilization for usage.

This glove may be used for either the dominant or non-dominant hand of the surgeon, other users may use the gloves individually or as a pair to perform other applicable functions. The glove should fit snugly and with comfort. The improvements allow for a puncture resistant material which is fashioned in one solid sheet at a thickness less than, equal to, or greater than those previously utilized. As a result, this invention is able to produce a glove with a thickness greater than those previously designed in areas not critical in tactile sensation which in turn provides greater puncture protection than those previously designed because it is a solid film which is impervious to body fluids and does not need additional films to act as the fluid resistant barrier. It can be of greater thickness in areas not concerned with tactile sensation due to the flex point and or wedge design. The glove's design allows for good flexibility and whose manufacturing process readily lends itself to mass production at relatively inexpensive costs to the consumer.

Another feature of the glove's design lies in its versatility. The design lends itself to be used with other materials entirely by themselves or combined with the preferred material, monofilament fishing line, or its equivalent, of which a component is nylon as a single layer or as a multithickness solid film or as a film with a coating whose properties serve different purposes such as chemical resistance, vapor resistance, thermal protection, electrical shock protection and other properties not previously mentioned.

The most striking difference between this glove and its predecessors is that one film whether it be of solely one material or a combination of materials provides the solid film barrier for resistance to exchange of body fluids and cut and puncture by sharp instruments. This significant difference enables the manufacture of a glove at the same thickness at the finger tip level as its predecessors, while providing more puncture resistant material because coatings or films do not have to be applied to prevent body fluid exchange. That is the significant and unique difference between my material and that of textured weaves used in the previous designs.

The palmar design can be constructed and then adhered by any means, including friction, to a latex glove (if so desired or required for unique applications), this concept is similar to those in the past, but the significant and unique difference is that the materials allow for greater puncture resistance because of increased thickness due to the flex point design and or stepped wedge design or tapered wedge.

These and other objects, features and advantages of the present invention are apparent within the following description when taken in conjunction with the accompanying drawings in which:

DETAILED DESCRIPTION

Figure 1:
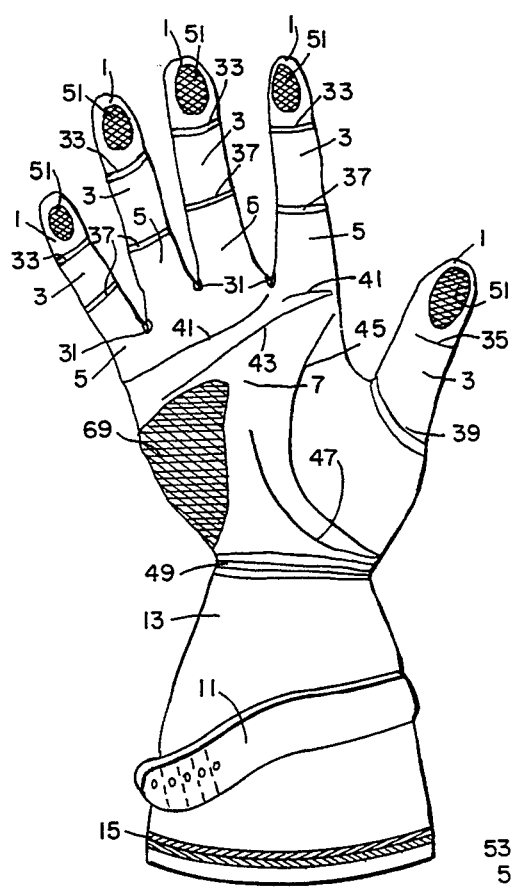
FIG. 1, depicts a view of right hand palmar surface with the preferred design.
Figure 2:
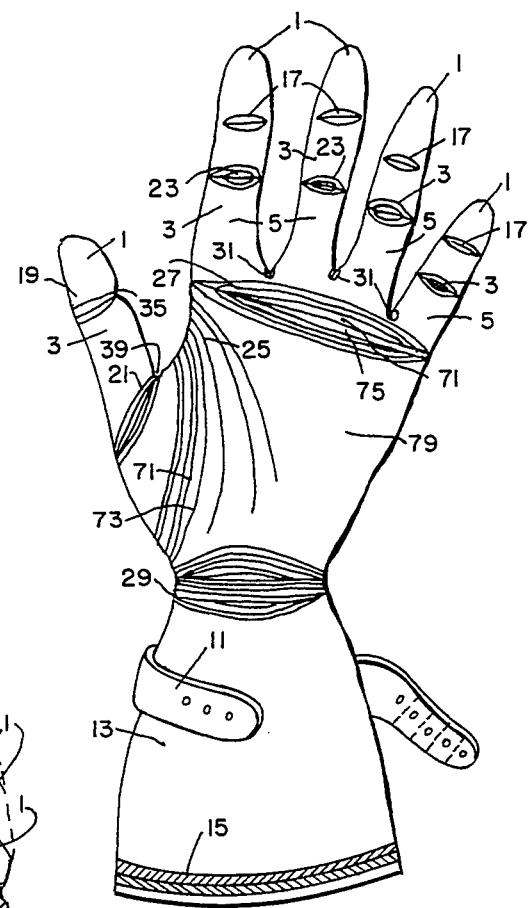
FIG. 2, depicts a view the dorsum of the right hand with the preferred design.
Figure 3:
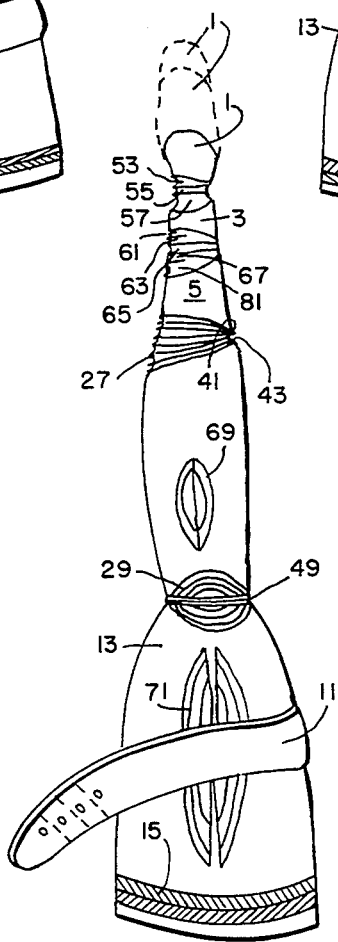
FIG. 3, depicts a side view of the lateral surface of the right hand with the preferred design.
Figure 4:
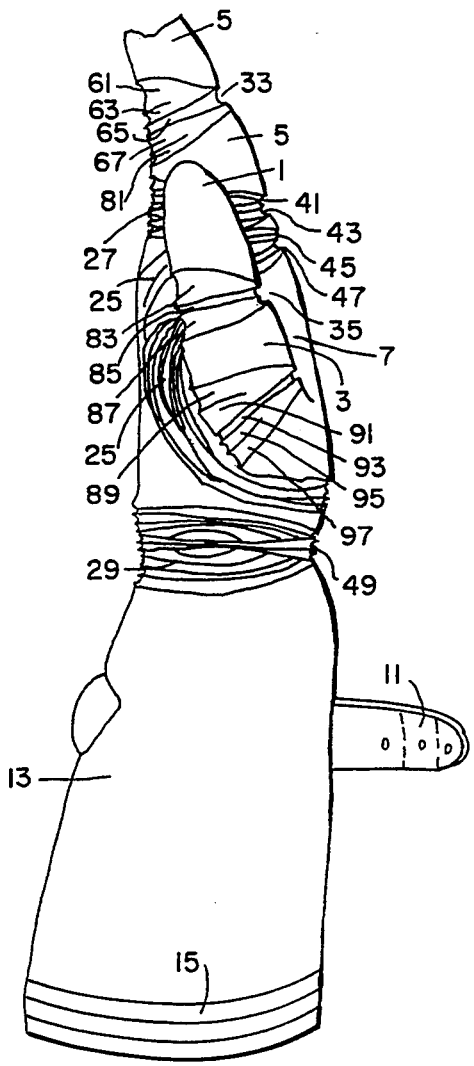
FIG. 4, depicts a side view of the medial surface of the left hand with the preferred design.

Notice how the fingers taper in the preferred design reflected by FIG. 1, FIG. 2, FIG. 3, and FIG. 4. The segments of each finger are attached to each other by the flex tubule (33) (37), each finger is attached to the palm by a flex tubule (41) (43), the thumb is attached to the palm by a flex tubule (39), and the palm is attached to the forearm by flex tubules at the wrist (49) and the glove is secured to the forearm by an adjustable strap (11) which is attached to the glove. The backide of the hand or dorsal surface (79) is attached to the acordion folds of the metacarpophalangeal joint (27) and the accordion folds of the wrist (29). At or near the end of the glove (the forearm segment) is the site for an additional closure mechanism (15) which may be embossed into the film or adhered to the inner or outer surface which could be utilized to secure the glove to the gown of an operator in such a manor that the glove and gown attached at the arm unit are one. The accordion expansion joints of the dorsum of the fingers (17) (23) and hand (27) (25) are obvious, the expansion joints provide expansibility for flexing the segment and attached the fingers to the palm (27). The thumb segments are attached to each other by the accordion folds (19) and the thumb is attached to the hand by the accordion folds (21). The hand is attached to the forearm by the accordion folds (29). These joints attached the segments of each finger to the next segment and the fingers to the hand. A strap (11) is evident which is to secure the glove to the forearm. Due to the fact that the thumb has a unique anatomical design and performs unique functions, special consideration is given to the design of the flex points to compensate for the compound actions resulting from flexing of the metacarpolphalangeal joint and the metacarpal trapezium joint of the wrist. FIG. 2, of the thumb shows not only the dorsal accordion folds (19) (21) (25), but a view of the lateral surface of the thumb. On this surface one sees that the accordion folds form an apex located at about the junction of the lateral surface with the palmar surface. This design is also present on the medial surface of the thumb. The mirror image of this same design, the dorsal accordion folds (19) (21) and its' apex at the midpoint of the joint, in which the folds meet at the junction of the palmar surface with the medial and lateral surfaces, a palmar flex tubule which is located at the midpoint of the joint (35) (39). The strap (11) which is one solid film. One portion of which has protuberances along its center which are pegs, taper shaped and the other portion of the solid film has tapered holes which are located along its' center which are slightly smaller than the pegs. The strap also is constructed with perforated break lines between the locking perforations to facilitate removal of excess strap. When the pegs and perforations are united, the strap locks and the pegs do not protrude beyond the perforations. The ovoid areas 51 of the distal segment 1 may be constructed of a thinner thickness of the film to allow greater tactile sensation, or the ovoid areas can have a film or embossed design to increase gripping ability, or construction can do both designs, dependant on need. These figures also depict other areas of the glove with designs (69) applied to increase gripping ability. The preferred design has an ovoid area embossed with a design which improves the operator's tactile ability and increased gripping and holding ability. The preferred number of accordion folds per joint are the following and depicted in FIG. 1, FIG. 2, FIG. 4, and FIG. 5a. The distal interphalangeal joints (17) three accordion fold total, the most distal fold (53) is arc shaped or curvilinear with the apex of the arc directed towards the finger tip. The first fold (53) is directed in a linear fashion at an angle of about 45 degrees in which the fold is directed in a dorsal distal direction and about the upper third or half of the medial and lateral surface, it arcs in a distal fashion so that the apex of the arc is directed distally and its apex is at the proper distance from the midpoint of the joint on the dorsal surface. The shape of the fold is the preferred bell curve. The second fold (55) is a bell curve and is straight, in essence, transecting the joint, and the third fold (57) is the mirror image of the first (53). The proximal interphalangeal joint accordion fold (23) consists of five folds. The first fold (61) mimics the first fold of the distal interphalangeal joint (53), the second fold (63) can extend to the apex created by the first and last folds or the fold does not have to extend to the apex, however, it must be present on the upper third or half of the medial and lateral surfaces as the dorsal surface. The fold is located at the preferred distance and is the preferred shape. If the fold does not go to the apex, the fold is curvilinear. If the fold extends to the apex, its appearance is the same as the first fold (61). The third fold (65) is a bell curve and is straight, which in essence transects the joint. The fourth fold (67) is the mirror image of the second fold (63) of this joint. The fifth curve (81) mimics the last fold of the distal interphalangeal joint (57). The metacarpophalangeal joints (27) consist of eight accordion folds. The first fold mimics the first fold of the distal interphalangeal joint (53). The second fold and third fold mimic the second fold of the proximal interphalangeal joint (63). The fourth fold (75) is straight and begins at the first metacarpophalangeal joint in essence as a flex tubule (41) travels to the medial surface of the hand, across the dorsum of the hand and around the fifth metacarpophalangeal joint and re-establishes itself as the flex tubule. After transecting the second metacarpophalangeal joint it terminates on itself in the second interspace of the hand. The fifth fold (77) at the fifth metacarpophalangeal joint, in essence as a flex tubule (43) and is directed laterally along the lateral surface of the hand, the fold is found on the dorsal and medial surfaces of the hand and then transects the first metacarpophalangeal joint and ends on itself at the distal third of the fifth metatarsal. The sixth and seventh folds mimic the fourth fold (67) of the proximal interphalangeal joint. The eight fold mimics the third fold of the distal interphalangeal joint (57). Special consideration must be given to the thumb, the interphalangeal joint (19) consists of three accordion folds the first (83) mimics the distal interphalangeal joints first fold (53), the second (85) is straight, the third (87) is mimics the third of the distal interphalangeal joint (57). The metacarpophalangeal joint (21) consist of five accordion folds arraigned is the same as that of the proximal interphalangeal joints (3) of the fingers. The first fold (89) mimics the first of the proximal interphalangeal joint (61), the second (91) mimics the second of the proximal interphalangeal joint (63), the third (93) is straight, the fourth (95) mimics the fourth of the proximalinterphalangeal joint (67), and the fifth (97) mimics the fifth of the proximal interphalangeal joint (81). The thumb because of its distinctive range of motion requires a flex point for the metacarpal trapezium joint (25). The flex point of this joint consists of eight accordion folds. The eighth accordion fold begins at the web space of the thumb and index finger. The first fold mimics the first accordion fold of the proximal interphalangeal joint (61) with this difference, at the upper half or third of the web space, it begins to arc eccentricly in a dorsal proximal direction and ends on itself on the dorsum of the hand short of the wrist. The second and third accordion folds mimic the second of the proximal interphalangeal joint (63) of the fingers with this significant difference, about the upper third or half of the web space they begin to arc in a eccentric fashion in a dorsal distal direction and end on themselves on the dorsum of the hand short of the wrist. The fourth and fifth folds are straight. The fourth fold (71) circumscribes the joint, travels around the thenar eminence as a flex tubule (45) and returns to it's point of origin. The fifth fold (73) follows the course of its mate and at a point beyond the area known as the anatomical snuff box it diverges from the course with its mate as a flex tubule (47) and follows a course to a point at about the center of the palm and ends on itself. The sixth and seventh folds mimic the second fold of the proximal interphalangeal joint (63) with this difference, their angle may be less than the 45 degrees and at the upper third of half of the web space, they arc back on themselves and in a curvilinear line end at a point past the anatomical snuff box. The first fold it mimics the fifth fold of the proximal interphalangeal joint (81) with this difference, its angle may be less than 45 degrees and at the upper third or half, it arcs in a dorsal proximal direction almost becoming straight and ends a place just past the anatomical snuff box.

The accordion folds of the wrist (29) are thirteen in number, the first fold is the same as the first fold of the distal interphalangeal joint (53). The next four folds mimic the second fold of the proximal interphalangeal joint (63). The next three are straight and transect the joint and mimic the middle fold of the proximal interphalangeal joint (65). The next four folds mimic the fourth fold of the proximal interphalangeal joint (67). The last fold mimics the last fold of the proximal interphalangeal joint (81). Note the mathematical sequence of the number of straight folds and the curvilinear folds. The web spaces of the fingers have three accordion folds (31) the folds are linear, have the preferred design, and their longitudinal axis is perpendicular to the palmar surface and extend from the junction of the palmar, medial and lateral surface at the metacarpophalangeal surface to the junction of the dorsal, medial and lateral surface of the metacarpophalangeal joint. The strap (11) in FIG. 1, FIG. 2, FIG. 3, and FIG. 4 is no greater than 5/64" in thickness and about 1" in width. The strap is attached to the glove as a single unit which contains a segment which consists of pegs along its center and another segment of the strap which contains perforations along its center. The pegs are 1/16" in median width and height, the perforations are full thickness of the strap and slightly less than 1/16" in width. Along the perforation strip portion of the strap, between the perforations are located breaklines which allow the operator to remove excessive strap. A second closure (15) is located at or near the end of the forearm segment. The seal is a locking strip is of the same dimensions of the strap (11). which creates a second means of preventing contamination of the operator with infectious material because it attaches the glove to the gown of the operator enabling the operator to remove the glove and gown safely as a one piece unit.

Figure 5A:
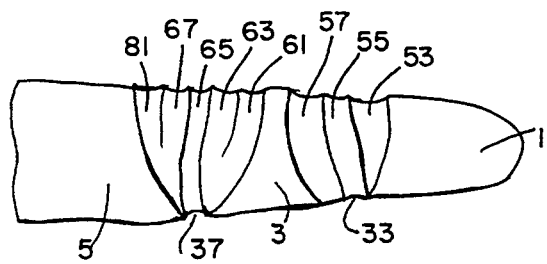
FIG. 5a, depicts a typical finger with the flex points of the preferred design.

FIG. 5a, depicts a close up view of a preferred flex point of the proximal and distal interphalangeal joints. The proximal interphalangeal joint is located between the proximal phalangeal segment (5) and the middle phalangeal segment (3). The distal interphalangeal segment is located between the middle phalangeal segment (3) and the distal phalangeal segment (1). The flex point consists of an accordion folds and the palmar tubule. The accordion fold of the distal interphalangeal joint consist of three folds. The first fold (53) is angulated at about 45 degrees to the palmar surface. It is linear in shape and extends in a dorsal distal direction. At about the upper half or third of the medial and lateral surfaces it becomes curvilinear and arcs across the dorsum of the finger. The apex of the arc is located at about the preferred distance from the midpoint of the joint. The second accordion fold (55) is straight and is located at the midpoint of the joint. The fold circumscribes the joint and on the palmar surface, it is the flex tubule of the joint (33). The third accordion fold (57) is angulated and is the mirror image of the first fold. The proximal interphalangeal joint flex point consists of five accordion fold. The first accordion fold (61), mimics the first fold of the distal interphalangeal joint (53). The second accordion fold (63) is curvilinear, does not have to extend to the apex created by the first and last accordion fold, the apex of its arc is located at the proper location on the dorsal surface of the joint and properly spaced between the first and third folds. The third accordion fold (65) is straight and has the same characteristics as that of the distal interphalangeal joint (55). The fourth accordion fold (67) is the mirror image of the second accordion fold (63). The fifth accordion fold (81) is the mirror image of the first accordion fold (57). at the four are angulated and one is straight. the The segment of the straight accordion fold which transverses the palmar segment of the glove is known as the palmar tubule.

Figure 5B:
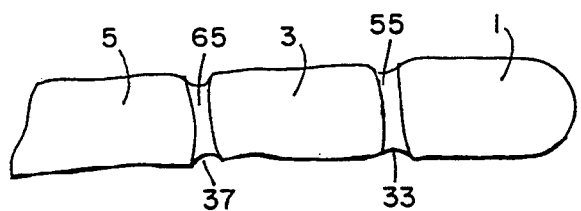
FIG. 5b, depicts a typical finger with the straight accordion fold of the preferred design.

FIG. 5b depicts the straight accordion folds of a typical finger of the preferred design. Notice how the segments (1) (3) (5) are attached to one another by the accordion fold (55) (63). The accordion fold on the palmar surface is the flex tubule (33) (37).

Figure 5C:
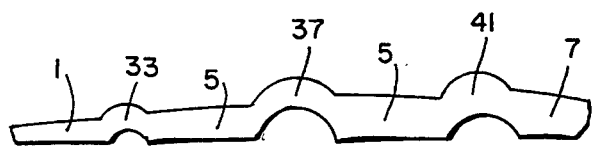
FIG. 5c, depicts a typical finger with the flex tubules and the stepped wedge design.

FIG. 5c depicts the palmar surface of a finger. Notice how the surface is continuous, the distal phalangeal segment (1) is attached to the middle phalangeal segment (3) by the flex tubule of the distal interphalangeal joint (33). The flex tubule is tapered in thickness to reflect the difference in thickness between segments (3) and (1) and is 1/16th" in depth. The flex tubule of the proximal interphalngeal joint (37) has the same characteristics as that of the distal flex tubule (33) and connects the palmar surface of the middle phalangeal segment (3) and the proximal phalangeal segment (5). The proximal phalangeal segment is attached to the palm of the hand (7) by the metacarpophalangeal joint flex tubule (41). This palmar tubule has all the qualities of the others with one variation, it is 2/16th" in depth.

A flex point is the area of the joint with the embossed preferred design applied. The preferred design consists of an accordion fold which is present on the dorsal, medial and lateral surfaces. One segment of the accordion fold is not angulated, it is a straight segment, this segment may circumscribe the joint, the portion of this fold which traverses the palmar surface is the flex tubule. The flex tubule does not have to be a part of the straight accordion fold, it can be a bell shaped curve located on the palmar surface of the glove. The flex point therefore consists of two segments, the accordion fold and the flex tubule.

As a generic overview of the accordion fold or flex point concept, the following explanation is offered. The accordion folds should have the following qualities. The first and last accordion folds should meet, the apex of the first and last fold is located about the center of the joint at the junction of the palmar, medial, and lateral surfaces. If the joint allows for motion in more than one plane, the first and last fold must meet at one midpoint of the joint at the junction of the palmar medial surface or palmar lateral surface along that plane. In a typical interphalangeal joint, the first fold is directed in a linear fashion at an angle of about 45 degrees in which the fold is directed in a dorsal distal direction and about the upper third or half of the medial and lateral surface, it arcs in a distal fashion so that the apex of the arc is directed distally and its apex is at the proper distance from the midpoint of the joint on the dorsal surface.

The straight accordion folds of the flex point do not necessarily have to circumscribe a joint if the joint has movement in more than one plane. In this case, it is necessary for the straight tubule to traverse the palmar surface of the joint, either the entire portion of the surface or a portion thereof.

Two straight folds may unite to form one tubule in which the singular tubule's characteristics are those of the preferred design.

The last fold is the mirror image of the first unless the motion of that joint occurs in more than one plane. The folds are curvilinear in design except those that are specified as being straight, if more than one straight fold is present, at least one must join the first and last fold at their apex, if only on straight fold is present, it must meet the first and last folds at both their apices.

The folds are embossed at an angle of 90 degrees into the full thickness of the film and may be tapered or angulated. The edges of the accordion folds are circular or a bell curve in shape, no sharp edges are present along the fold. The flex point may be a combination of geometric shapes.

The folds are equally spaced along the joint, and if any film is located between the folds, it has no design imparted to it. The flex points may be placed before or after the joint, in the preferred design the flex point is located about the midpoint of the joint. The distance between the apices of the first and last arcs of the accordion folds which span the joint in the preferred design is the following: ¼" for the distal interphalangeal joint and interphalangeal joint of the thumb, ½" for the proximal interphalangeal joint and the metacarpophalangeal joint of the thumb, ¾" for the metacarpophalangeal joint and the metacarpal trapezium joint of the thumb, and 1¼" at the wrist. The preferred design of the accordion folds is that of the bell curve.

A number of methods and designs are feasible. The preferred method will provide the least expensive means which can produce the highest quality product.

The preferred material is monofilament fishing line or its equivalent or nylon as the cut and puncture resistant material. The preferred material or nylon may be combined with or substituted with polymers, co-polymers, resins, aramids, fiberglas, acrylics, cyanoacrylics, ceramics, carbon fiber, salts, metals, composite materials, and other puncture resistant materials. The material may take shape or form as a single homogeneous film, or a blend of materials. The glove should be of excellent construction, materials and not fit sloppily on the hand(s) of a surgeon.

Weaves, filaments or fibers which are bonded together by chemical bonding or any other means will result in a the non-porous material which I hereafter describe in my invention.

When a solid sheet of nylon or the preferred material has heat and pressure applied to it. The resultant solid sheet of material takes the shape of the object it is pressed into. When allowed to cool in this shape, the design is retained by the material. If a deforming force is applied to the material, such as elongation of a hollow geometric shape or portion of a geometric shape such as bell curve or almost complete circle, the material deforms. When the deforming force is removed from the material, the material returns to its original shape.

The material may or may not take shape as a smooth solid film, for example the solid film may have a geometric or partial geometric surface contour such as a series of semicircular halves bonded together in a solid sheet.

The material has memory and this inherent quality can be utilized to aid my designs ability to lengthen and shorten because the material returns to its original shape when the deforming force is removed. Thus, a relatively stiff material becomes more flexible because the material's ability to bend on itself is facilitated with my designs. The quality of the stiffness is what gives the glove its ability to withstand cutting and puncturing.

The preferred design for the flex points of the glove are as follows. In my description of the accordion folds for each joint, I will call them by number, the most distal fold or the fold closest to the finger tip is the first accordion fold, the last accordion fold is the most proximal or the fold which is closest to the cuff of the accordion folds.

The folds should have the characteristics which have previously been stated. The accordion folds for the joints are 1/16th" in height and width, they are bell shaped curves, they are embossed the full thickness of the film with the mean chord of the curve at an angle of 90 degrees to the film. They are linear and curvilinear or taking the shape of an arc which span the medial, lateral, and dorsal surface of the joint. Three accordion folds are present at the distal interphalangeal joint. The first fold begins at about the midpoint of the joint at the junction of the palmar surface with medial and lateral surface of the joint. The second fold spans the joint and is straight, it begins at the junction of the palmar surface with the medial and lateral surfaces. The third fold begins at the junction of the palmar surface with the medial and lateral surfaces of the joint about the midpoint of the joint. The first and third folds meet at the approximate center of the joint at the junction of the medial and lateral aspect of the joint. The first and third folds extend from the apex at an angle of about 45 degrees from the palmar surface, the first fold is directed in a dorsal distal direction to the upper third or half of the surface, at about this point the fold begins to arc with the apex of the arc directed distally, the last fold is the mirror image of the first. On the palmar surface of this joint is located about its midpoint a flex tubule, the flex tubule is a bell curve in shape, 1/16th" in diameter and height which has been embossed at 90 degrees into the full thickness of the film, in essence it is the palmar portion of the straight accordion fold of the joint. The mean chord of the bell curve is perpendicular to the palmar surface.

The proximal interphalangeal joint consists of five accordion folds, the first two are distally, the third is straight, and the last two are cuvilinear with the apex of the curve directed proximally. The first and last fold are the same design of the distal interphalangeal joint, the second and fourth folds do not extend to the junction of the palmar surface with the medial and lateral surfaces, they are curvilinear and traverse the entire dorsal surface and end on the upper third or half of the medial and lateral surfaces. The second fold has the apex of the arc located on the dorsal surface directed distally and about equidistant between the first and third folds. the fourth fold is the mirror image of the second fold. The folds are 1/16" in height and width, 90 degrees to the film, and are embossed full thickness into the film. The palmar flex tubule is the same as that of the distal interphalangeal joint. The medial and lateral surfaces of the fingers should be concaved the dorsal and palmar surfaces may be slightly concaved and the fingers should taper with the widest portion of the finger located at the metacarpophalangeal joint and the narrowest at the distal phalangeal segment.

The web spaces of the fingers have three accordion folds the folds are linear, have the preferred design, a film thickness of 0.007", and their longitudinal axis is perpendicular to the palmar surface and extend from the junction of the palmar, medial and lateral surface at the metacarpophalangeal surface to the junction of the dorsal, medial and lateral surface of the metacarpophalangeal joint. The web spaces of the fingers must have three accordion folds to accommodate the abduction and adduction of the fingers. The longitudinal axis of the ribbing or accordion folds should connect with the dorsal and palmar surfaces. They shall be have the same characteristics as those of the preferred design.

The metacarpophalangeal joint accordion folds are eight in number and the first three arc distally, the middle two are straight, and the last three arc distally. The first and eight folds are the same as the first and fifth folds of the proximal interphalangeal joint. The middle two folds extend to the junction of the medial and lateral surfaces with the palmar surface with this significant difference. The fourth fold is straight and begins at the first metacarpophatangeal joint in essence as a flex tubule travels to the junction of the palmar and medial surface of the hand, across the medial and dorsum of the hand as a straight accordion fold and then around to the lateral surface of the hand and at junction of the lateral and palmar surfaces at the fifth metacarpophalangeal joint re-establishes itself as a flex tubule. After transecting the second metacarpophalangeal joint it terminates on itself in the second interspace of the hand. The fifth fold forms on the palmar aspect of the fifth metacarpophalangeal joint, in essence as a flex tubule and is directed laterally along the lateral surface of the hand where it is a straight accordion fold. The staight fold is found on the dorsal,medial, and lateral surfaces of the hand and at the junction of the palmar and medial surfaces becomes a flex tubule once again, then transects the first metacarpophalangeal joint and ends on itself at the distal third of the fifth metacarpal. When one flexes their palm to its maximum, the two tubules are adjacent to one another, in essence, they become one. The second and third folds mimic the second fold of the proximal interphalangeal joint. The sixth and seventh folds mimic the forth fold of the proximal interphalangeal joint. The folds are 1/16" in height and width, 90 degrees to the film, and are embossed full thickness into the film. The palmar flex tubule's design is the same as that of the proximal interphalangeal joint with this difference, the width and height of the tubule is 2/16th".

The design of the thumb's interphalangeal joint is the same as that for the distal interphalangeal joints of the fingers. The design of the metacarpophalangeal joint of the thumb is the same as that of the proximal interphalangeal joints of the fingers. Due to the unique ability of the thumb to oppose the little finger, in which, the motion occurs at the metacarpal trapezium joint, a flex point must be placed at that joint to accommodate the motion. The joint should have eight accordion folds with an unique arrangement to accommodate for the particular action of allowing the thumb to joint to appose the little finger. Since it is impossible to place the accordion folds for the thumb adjacent to each side of the joint, it is necessary to have a place of origin or termination of the folds in the area of an imaginary line which would mimic the position of a line through the joint. The first, second, and third accordion fold begins at the web space of the thumb and index finger and mimics the first, and second accordion folds of the proximal interphalangeal joint with these exceptions, their arc is eccentric in nature and they end on themselves on the dorsum of the hand. The fourth and fifth folds are straight. The fifth fold follows the course of its mate and at a point beyond the area known as the anatomical snuff box it diverges from the course with its mate as a flex tubule and follows a course to a point at about the center of the palm and ends on itself. The fourth fold circumscribes the joint, travels around the thenar eminence as a flex tubule and returns to it's point of origin. The sixth and seventh mimics the fourth fold of the proximal interphalangeal joint with this difference, the angle may be less than 45 degrees the arc of the curves is much flatter, almost straight and end at a place on the hand just beyond the anatomical snuff box. The eighth accordion fold mimics the fifth fold of the proximal interphalangeal joint with this difference, the angle may be less than 45 degrees, the arc of the curve is flatter, almost straight and ends at a place on the hand just beyond the anatomical snuff box.

The palmar surface of the palm should be contoured in such a manner resembling one's palm. The medial and lateral surfaces of the palm should be concave with the concavity directed away from the operator's skin. The palmar flex tubules of the palm are placed to allow for apposition of the thumb with other fingers and to allow one to grip an object.

The accordion folds of the lateral surface of the palm are five in number, they may linear or curvilinear. They begin in an area which corresponds to the proximal portion of the metacarpophalangeal joint and extend distally to an area just before the wrist, the arc apex of the folds are directed towards the junctures of the dorsal and palmar surfaces of the glove. Accordion folds are located along the lateral border of the palm and stops short of the accordion fold for the metacarpophalangeal joint and the wrist to accommodate for any expansion of the hand when making a fist. They have the same characteristics as the other accordion folds of the glove. The accordion folds are $\frac{1}{8}$th" in size, and the first two folds arc dorsally. the third is straight, and the last two arc palmarly.

The wrist has thirteen dorsal accordion folds, the first five folds arc distally, the next two are straight, and the last five arc proximally. The accordion folds are 3/16" in size. The folds are constructed in the same fashion as that of the other joints, in which the first and last fold must join together at the junction of the palmar surface with the medial and lateral surfaces. Three palmar tubules are present, they are 3/16th" in size, embossed at 90 degrees to the surface, they are evenly spaced on the palmar surface of the wrist, the first and last tubule are about $1\frac{1}{4}$" apart.

Eight accordion folds are located on the lateral surface of the forearm which extend from a point just before the wrist and end at a point about 1-$1\frac{1}{2}$" from the second closure mechanism. The folds are 3/16th" in width and height, they are embossed full thickness into the film, they are bell curves with the mean chord of the figure at 90 degrees to the film. The folds begin about 1/16th" from the accordion folds of the wrist and may terminate at the end of the glove if a second closure mechanism is not employed. The preferred design has a second closure mechanism.

The flex point designs of the glove may be coated with a non-toxic, non-stick material which enable them to remain free of any debris, since debris can interfere with the flexion mechanism.

The cuff is tightened by use of a tab system similar to that of adjustable hats. The straps attachment to the glove may be by any means or be embossed from the glove itself, the preferred means is to have the strap attached to the glove. The strap is about 5/64" in thickness and about 1" in width. The strap is attached to the glove as a single unit which contains a segment which consists of pegs along its center and another segment of the strap which consists perforations along its center.

The pegs are 1/16" in median width and height, the perforations are full thickness of the strap and slightly less than 1/16" in width. This allows for the strap to stay securely closed. Along the perforation strip portion of the strap, between the perforations are located break lines which allow the operator to remove excessive strap. Small soft flexible loops may be attached to the outer surface of the forearm to help keep the strap in its proper location. On the inside surface of the glove, at the same location as the strap is an attached a pliable conforming film which may circumscribe the forearm segment or be located along the longitudinal axis of the forearm. The soft pliable film located beneath the strap is wider than the strap. The seal may also take the form of a sealed cavity or bladder which may be adhered to the inner or outer surface or formed within the layer of the forearm segment in which air may be injected into the chamber via a pump which is inflated by the operator with and adjustable valve to create a fluid resistant barrier by pressure. The air bladder can be adhered to the inner surface of the glove by welding and or adhesives. The pump is located on the inner or outer surface of the forearm and the bladder is inflated prior to the second closure mechanism is sealed. If the air pump were located on the outer surface, it would have to have a connection through the forearm film to the bladder. The location of the sealed cavity may be at a location other than that of the adjustable strap. The area on the forearm could contain two seals, one of which is very flexible and would prevent seepage of fluid into the glove at or near the end of the forearm segment of the glove. A second seal which could be either embossed full or partial thickness of the forearm segment of the glove's film or attached to the forearm and could be in the form of a seal similar to that of a zip lock bag which would interlock with its mate on the forearm of the operator's sleeve of the gown or protective clothing. Alternatively, the second seal can be of any reconfiguration of the seal and use any material which insures full closure of the glove with the operators gown or protective clothing. This mechanism would then create a body fluid barrier resistant suit. The preferred seal is attached to the glove. This type of suit would allow the operator would remove the glove and gown as one unit in which the operator's skin would not come into contact with any body fluid debris and or infectious material. This type of configuration could be applied for other purposes such as an environmental accident cleanup suits.

The design imparted to the joints of the fingers and hand is of extreme importance. The problem which exists with nylon is that nylon is a relatively stiff. Flexing the finger, demands that the dorsal surface must extend in length and the palmar surface must shorten in length. The solution to the problem is to allow for that shortening and lengthening to occur at the joint area. Incorporating the flex point design with the stepped or tapered wedge design allow for this to occur. These elongation and shortenings can occur with the flex point design alone. The tubular or rib or accordion design of the dorsum of the fingers and hand allows for extension of that surface, and the tubular design of the palmar aspect of the fingers and hand allow for contraction of the material. The medial and lateral surfaces of the fingers, thumb, and wrist also must have the ability to lengthen and shorten utilizing a stiff or somewhat stiff material. The design for the medial and lateral surfaces of the fingers and hand is incorporated in the preferred design imparted to the joint areas (the flex points). These designs allow for the elongation and shorting of the surface as tested and proven using an acrylic to define the significant lines of stress resulting from finger flexion.

The test results demonstrated that the dorsal medial surface of the finger elongates and the palmar medial aspect of the finger shortens. The test lines also curved in an arc shape with the apex of the arc directed dorsally. This observation is extremely critical when dealing with stiff materials more so than when dealing with somewhat flexible or flexible materials. An acrylic or latex glove has the ability to extend to lengthen and when subjected to compound stress. Nylon and other stiff materials does neither. If the lengthening and shortening of the surface is not properly addressed, the stiff material with either bulge grossly out away from the finger in a fashion which is unacceptable, or will inhibit the ability to flex the joint. These problems were demonstrated with the acrylic glove and these problems were overcome with my preferred design.

The preferred sizes of the flex tubules are 1/16th" for the distal interphalangeal joint, 1/16th" for the proximal interphalangeal joint, 2/16th" for the metacarpophalangeal joint and the palm, and 3/16th" for the wrist, the thumb flex tubule is 1/16th" for the interphalangeal joint and 2/16th" for the metacarpophalangeal joint. Alternatively, the flex tubules can increase is size going from 1/16th" at the distal interphalangeal joint, ⅛th" at the proximal interphalangeal joint, and 3/16th" at the metacarpophalangeal joint or be totally variable.

A straight accordion fold may have all or part of the same width and depth as its flex tubule. The angulated tubule may have the same width and depth as to the flex tubule it joins. The depth of each palmar flex tubule may be greater than its' width. The preferred shape of the flex tubule and its angulated counterparts is that of the bell curve.

The bell curve should be tapered in thickness to insure coincidence with the adjoining segments thickness. Concurrently, the palmar surface should maintaining a constant thickness and the walls of the medial and lateral surfaces should be tapered to insure coincidence of all surfaces and segments. The flex tubule design is embossed in the full thickness of the film in the preferred design. In the preferred design, the flex tubule circumscribes the joint, and functions as one of the straight accordion folds.

The glove can be constructed with some or all alternate design(s) replacing the preferred design, or in combination with some or all other alternate design(s). All or some of the following modifications can be made to the preferred design.

In an alternate design of the flex tubule, the flex tubule is located behind the midpoint of the joint and does not function as the straight accordion fold. The palmar flex tubule may have variations, they include angulated tubules which may be constructed at an angle other than 45 degrees to the palmar surface, they are embossed the full thickness of the film and are a tapered bell curved in shape. They may extend along the dorsal, medial, and lateral surfaces in a distal dorsal direction away from the palmar flex tubule. If they extend only along the medial and lateral surfaces, they terminate about the center of the longitudinal axis of the surfaces wherein the dorsal accordion folds are constructed to compensate for the angular deflection. A mirror image of the anteriorly directed tubule can be present. The tubule may be embossed anywhere along the palmar surface away from the flex point area. The flex tubule may be a combination of geometric shapes. These additional tubules are not found in the preferred design, they may be used as enhancements in alternative designs. Alternatively the flex tubule can be of the thickness of the thinner segment, the thicker segment, a thickness which is a combination of both the thicker and thinner segment, or a constant thickness.

In an alternate design, a concentric circle design is utilized, circumscribing the flex points, the spacing between concentric circles and the depth of the resultant ridges should cumulatively approximate the length that the surface must shorten or lengthen. The material, nylon is stiff, however, concentricity similar ridging as in a "soda fountain" straw provides the degree of flexibility required to achieve acceptable levels of dexterity. The interesting quality of nylon is that it has memory in which it returns to its original shape when the deforming force is removed. Thus the material has the ability to move on itself when a deforming force is applied and it returns to its original shape due to the material's memory. With utilization of the variety of flex point designs and the wedge designs, there is increased ability to bend a stiff material. In the preferred design, the mean chord of the geometric shape is embossed at a 90 degree angle into the film. Alternatively, the mean chord of all geometric shapes or portions thereof may be embossed at an angle other than the 90 degree angle may be substituted for preferred geometric shape, the tapered bell curve.

In an alternate design, the flex points of the fingers thumb, and wrist can be formed with one or more accordion fold(s) which can completely encompass the joint or a part of the joint the same thickness of that of the adjacent distal thickness or that of the thickness of the distal portion of the finger (for example, the thickness of the ribbing of the proximal phalangeal joint is 0.021" in thickness or 0.007" in thickness) or all the flex points may be of the thickness as that of the distal segment, 0.007". The height of the rib would be approximately 1/16" in which the ribbing can completely encompass or partially encompass the joint and can be with the convexity directed either away from the operator's skin surface or with the concavity about 1/16" directed towards the operator's skin surface, the convexity and concavity does not protrude or if it does it does not protrude significantly so that the exterior surface of the glove is relatively flat.

The preferred thickness of the glove are 0.007" for the distal phalangeal segment, the medial and lateral surfaces of the glove, the dorsal surface of the glove, the middle phalangeal segments and the proximal phalangeal segment for the thumb are 0.014" in thickness. The proximal phalangeal segments of the glove are 0.021" in thickness as well as the thenar eminence. The palm of the glove is 0.035" in thickness. The forearm portion of the glove is 0.055" in thickness. This design is the stepped wedge, in a tapered wedge, the same measurements and relationships exist for the median chord of each segment. Alternatively, all the surfaces of the glove can be of one thickness or they may have any combination of thicknesses or the palmar surface can differ from the preferred design.

The glove can be constructed with some or all alternate design(s) replacing the preferred design, or in combination with some or all other alternate design(s). All or some of the following modifications can be made to the preferred design.

Alternate design one of the flex point; the accordion folds meet at the junction of the medial and lateral surfaces with the palmar surface, they have all the characteristics of the preferred design. The apex of the accordion folds is located about the center of the joint. The flex tubule is located behind the midpoint of the joint at a position in which the apex of the accordion folds can move proximally towards the wrist or immediately behind the apex. The palmar flex point has all the characteristics of the preferred design. The pie shape of the accordion ribs encompasses the entire joint, this design allows for the extension of the dorsal surface and the extension and shortening of the medial and lateral surfaces.

In alternate design two of the flex point; the joint is one in which the flex point circumscribes the joint as in the preferred design, and the accordion ribbing extend from one central point starting at the midpoint of the joint and about the middle of the longitudinal axis of the medial and lateral surfaces. All other components of this design have the characteristics of the preferred design.

In alternate design three of the flex point; the preferred design is embossed into the joint. In the area of the glove which would correspond to that of the phalangeal shaft, accordion folds are placed on the medial and lateral surfaces of the glove to accommodate the lengthening and shortening of those surfaces of the glove in finger flexion. The folds may be at 90 degrees to the dorsal and palmar surfaces or angulated to the dorsal and palmar surfaces but extend to the junctions of the dorsal and palmar surfaces or along the longitudinal axis of the medial and lateral surfaces. The accordion fold may be linear or curvilinear along to its longitudinal axis.

In alternate design four of the flex point; a palmar tubule can be place behind the joint and a series of accordion folds are placed before it. The accordion folds are concave in shape and extend totally around the joint.

In alternate design five of the flex point; a flex point may extend from the palmar aspect of the joint as an expanding accordion fold which extends dorsally and distally away from the midpoint of the joint at an angle of 45 degrees, as the tubule moves further from the junction of palmar medial and lateral surface, the tube widens. The broadening tubules proximal fold makes an angle of 30 degrees with the distal edge of the straight tubule. A mirror image is found on the posterior edge of the straight tubule. This design may have a palmar surface tubule which may be located just behind the flex point.

In alternate design six of the flex point; the flex point is that of a figure eight where the upper and lower segments meet at the about the center of the joint on the medial and lateral surfaces and an offset figure eight in which the bottom portion of the figure may be in front of or behind the upper portion. An additional flex tubule may be placed behind the lower segment. All other characteristics of the flex point are of the preferred design.

In alternate design seven, the accordion folds may pressed back on themselves. The rational behind this is that more material can be gathered between the folds which may decrease the number of folds necessary to have an adequate amount of material for joint expansion. It is important to understand that a sheet of nylon if pulled does not stretch to allow for lengthening or expansion. If the same sheet of nylon is gathered in folds, it will lengthen. If a series of folds are gathered in such a manor in which they are tapered to one point, the material will bend in an arc.

In alternate design eight, an alternate design of the flex point may consist of a combination of both concave and convex or solely concave or convex ribs may be utilized at the flex points of the glove, their appearance would resemble that of a FIG. 8, with the meeting of each rib in about the center of the medial and lateral sides of each joint. An alternate FIG. 8 design can be used in which the FIG. 8 is offset with the lower segment placed before or after the upper segment. The dorsal ribbing is offset from the palmar ribbing and a flex point (tubule) is placed behind the palmar ribbing. The purpose of the palmar tubule is to allow the compressed ribbing to get tuck out of the way so the surface can be flatter so as not to interfere with instruments, the fold may be tucked inside the glove so that the outside surface of the glove is relatively smooth and that the area of the tucked folds will buldge slightly. A palmar tubule may also be utilized with the FIG. 8 design. With the dorsal and palmar tubules offset, the palmar tubule is located just behind the head of the phalanges or about the midpoint of the joint, the purpose for this is to allow for the shortening nylon to go somewhere, the tubule can be circular or another geometric form in shape, and when the ribbing of the palmar surface the ribbing as it folds upon itself will not bulge and the use of instruments is less encumbered. The hollow tubule or flex tubule located on the palmar surface may be adhered to the inner surface of the palmar surface in such a manor where the tube meets the surface and the adherence may be at either side of the circle, preferably, at the proximal portion of the circle, the circle modified to an oval and this would facilitate the ability of the tube to retract with the shortening of the palmar surface with finger flexion. The flex tube may be placed before the joint, as an alternative design if the flex tube behind the joint is unsatisfactory. An alternate design of the FIG. 8 design which allows for only a portion of the hand to lengthen while the contralateral portion remains intact. A combination of both concave and or convex ribs may be utilized at the flex points of the glove, their appearance would resemble that of a FIG. 8, with the meeting of each rib in about the center of the medial and lateral sides of each flex point. Another alternate design is one in which the palmar flexion ribs are at full extension or almost full extension when the finger or hand is straight.

The first alternate design for the thumb; the interphalangeal joint of the thumb is the same as the proximal interphalangeal joints of the fingers. The reason for this is that the range of motion of the thumb, as a whole, is unique. The second reason for this difference is that the thickness of the palmar surface is equivalent to that of the middle phalanx of the fingers. The thickness of the material at the distal segment may cause need for additional flexibility. The metacarpophalangeal joint of the thumb the joint has eight accordion folds. The first accordion fold is the same as the first fold of the interphalangeal joint. The second fold extends to the apex created by the first and the third fold (the straight fold), the next five folds due to the uniqueness of the thumb's range of motion then begin at the apex on the web space of the thumb and index finger and arc eccentrically across the dorsum of the hand and end on themselves at a point short of the wrist.

The second alternate design for the thumb; the interphalangeal joint has three accordion folds with the characteristics as the distal interphalangeal joints of the fingers. The metacarpophalangeal joint of the thumb has five accordion folds with the same characteristics as that of the proximal interphalangeal joints of the fingers. The metacarpal trapezium joint has three accordion folds, in which the first fold is angulated as in the preferred, the second is straight and circumscribes the joint, and the third is angulated and mimics the first fold.

In alternate design one for the metacarpal trapezium joint for the thumb, all the characteristics for the joint are as in the preferred design with the modification of the first straight fold, it ends on itself near its place of origin.

In alternate design two for the metacarpal trapezium joint for the thumb, all the characteristics for the joint are as in the preferred design with the modification that the point of origin of the folds may be adjacent or at the metacarpophalangeal joint folds.

In alternate design three for the metacarpal trapezium joint for the thumb, all the characteristics for the joint are as in the preferred design with the modification that all angles for the angulated tubules can vary from 45 degrees and that the number of eccentric arcing folds may vary.

The flex points for the alternate designs of the thumb should have the characteristics as the preferred design. The preferred, and the two alternate designs of the thumb can have their apices located at the metacarpal trapezium joint and the eccentric folds extend from that point and rejoin at the web space or end on themselves.

The first alternate design of the metacarpophalangeal joint has eight accordion folds. All of their characteristics are that of the preferred design. The first three folds, the fifth fold, and the last three folds are that of the preferred design. The fourth fold begins as a flex tubule at the first metacarpophalangeal joint. It follows the same course as in the preferred design but ends on itself at the palmar surface of the web of the index and middle finger.

The second alternate design of the metacarpophalangeal joint has eight accordion folds. The design has all of the characteristics are that of the preferred design. The first three folds, the fifth fold, and the last three folds are that of the preferred design. In this design, the fourth fold does not end on itself, but as the middle fold of the web space of the index and middle fingers.

The third alternate design of the metacarpophlangeal joint has eight accordion folds. All of their characteristics are that of the preferred design. The first three folds, the fourth fold, and the last three folds are that of the preferred design. The fifth fold is the same as the straight fold of the proximal interphalangeal joint.

The fourth alternate design of the metacarpophalangeal joint, has eight accordion folds. All of their characteristics are that of the preferred design. The first three folds, and the last three folds are that of the preferred design. The fourth fold ends at or in the web space and the fifth fold circumscribes the joint.

The fifth alternate design of the metacarpophalangeal joint has eight accordion folds. All of their characteristics are that of the preferred design. The first three folds, and the last three folds are that of the preferred design. The fourth and fifth folds mimic the third fold of the proximal interphalangeal joint.

In an alternate design of the web space accordion folds, the number and axis of folds may vary which includes the web space between the thumb and index finger.

In an alternate design of the accordion folds on the lateral aspect of the palm of the hand, the number, and longitudinal axis of accordion folds can vary from the preferred design.

In an alternate design of the accordion folds of the forearm, the number, location, and longitudinal axis can vary.

In an alternate design of the palmar tubules located on the palmar surface, the tubule may be adhered to the inner surface of the palmar surface in such a manor where the tube meets the surface and the adherence may be at either the proximal or distal portion (the beginning or end) of the bell curve, preferably, at the proximal portion of the curve.

The flex tubule may be placed before the joint, if the flex tube behind the joint is unsatisfactory.

The glove could be constructed with the palmar flexion ribs are at full extension or almost full extension when the finger or hand is straight, this design could diminish any excessive mishapening of the glove.

In an alternate design of the finger segment, the area of the joints may be wider than the phalangeal shaft portion of the finger, the reason for this is that anatomically, the joints are the widest portion of the finger, they are wider than the shaft portion of the fingers. The flaring of the joint area should begin at about the proximal and distal third of the two phalanges which compromise a joint. The flare should be genteelly tapered and not obtrusive, the flare can encompass all surfaces or any combination of surfaces of the finger joint. The same type of flaring can occur at the level of the metacarpophalangeal joints. A second reason for this is that with the fold of the flex point directed inward towards the operator's skin, after a long while, if the glove is tightly fitting at this area, the edge of the accordion fold could become uncomfortable. Since the depressed potion of the film is 1/16th", of the increase in size is by that much, greater comfort can be had by the operator. All thicknesses after the taper are not sharp to include that of the flex point, and all surfaces of the segment.

In an alternate design which may increase the flexibility, the joint may have the accordion folds along the outside surface of the medial, lateral, and dorsal surface and are embossed the full thickness of the material. The height of the folds are approximately 1/16". If the folds are not located at the joint level, they may be placed before or after the joint along the medial and lateral surfaces of the fingers and hand to accommodate the lengthening and shortening of those surfaces. The folds may be used in conjunction with the flex point and/or wedge designs. The longitudinal axis of the folds may be at 90 degrees or less to the dorsal and palmar surfaces, and they be linear or curvilinear. The design would allow for the flexion necessary to flex a finger, however the design may interfere with instrument use. The accordion folds may pressed back on themselves. The rational behind this is that more material can be gathered between the folds which may decrease the number of folds necessary to have an adequate amount of material for joint expansion. It is important to understand that a sheet of nylon if pulled does not stretch to allow for lengthening or expansion. If the same sheet of nylon is gathered in folds, it will lengthen. If a series of folds are gathered in such a manor in which they are tapered to one point, the material will bend in an arc.

The palmar surface of the glove in the preferred design is contoured. An alternate design of the surface is to have it appear flat. Another feature which can be incorporated into the design is to have the surfaces of the fingers and palm mimic that of one's hand. Surfaces of the glove can be concave and convex where appropriate, rather than being that of a flat surface.

The design of a solid material of the type which I have previously described and hereafter describe may be adhered to another material by any means including friction.

The pads located on the distal phalanges of the fingers can be comprised of other materials which will increase the tactile sensation while reducing the puncture resistance, as example of this would be latex. The pads can be comprised of a soft material such as polypropylene, which does not have as great puncture resistance as that of nylon, but its puncture resistance may greater than that of latex. If the pad designs were incorporate into the glove, they would be ovoid in shape and may or may not cover the entire palmar surface of the glove. A different geometric design can be utilized and it may or may not cover the entire surface of the distal segment of the glove. The preferred design is ovoid with the area embossed with a design to improve tactile sensation along with improving gripping ability. In the alternate design, the ovoid area is 0.007" or less of cut and puncture resistant material and the entire palmar segment of the distal segment is embossed with a design to improve gripping ability. The finger pad areas can be composed of another material (which would be ovoid in shape and does not extend over the entire palmar surface of the finger, the balance of the flexion area of the palmar surface of the distal segment would be that of nylon) which would be substituted for the nylon which would provide with about the same cut and puncture resistance as that of nylon but be of greater flexibility. The design allows for the distal segment to be of increased thickness than the preferred design, and the ovoid area on the tactile pad of the finger to be of thinner material so there is greater puncture resistance on the distal segment of the finger and the area of tactile sensation is not compromised.

An alternative design of the glove would be to use the same cut and puncture resistant layer of the mesh as Seid used, and emboss the flex point and/or wedge design into the mesh. The mesh could be increased in thickness as one moves proximally away from the distal phalanx and incorporating the flex design and/or the stepped wedge design. The flex point area could be fused by simply phenol or heat application and pressure embossing. The advantage of this is that the glove would have greater flexibility and cut and puncture resistance, the ribbing on the dorsal surface would not be as great or eliminated if the dorsal surface was of another material of greater flexibility other than nylon. Less attention would have to be directed at the designs of the dorsal, medial, and lateral surfaces of the glove, because the use of latex, a very flexible material would be utilized. If the mesh were to incorporate the medial and or lateral surfaces, then a flex point design which would accommodate to the nylon material may be necessary. The major disadvantage of this method is that the nylon layer would not be impervious to liquids and must be sealed by another material, whereas in my design, no additional film is necessary to created a body fluid barrier.

An alternate design of the glove would to utilize the palmar surface of the glove or any other surface of the glove, emboss the flex tubule and/or wedge design and adhere it by any means to a latex glove including friction. Any of the other surfaces of the invention may be added or substituted for the palmar surface. Any of the preferred designs and any and all designs of this invention may be incorporated into this glove. In this instance, the preferred material of the ovoid area of the distal segment may be substituted with latex.

An additional unique feature of this glove design is the stepped thickness of the materials where the Fibanacci relationship is maintained to provide the maximum mechanical advantage. In this instance, the distal phalanx is 50% in thickness of the middle phalanx, the middle phalanx is 66% in thickness of the proximal phalanx, and the proximal phalanx is 60% as thick as the palmar surface. The increasing in the thickness of the material follows a mathematical progression. As on moves from the finger tip towards the palm the next segmental thickness is arrived by adding the preceding two thicknesses, in essence, a Fibanacci relationship. The wedge design gives mechanical advantage to the distal portion of the finger which in turn give the distal segment of the finger the mechanical advantage to help push the material on itself so that the compensation for the shortening can occur at the flex point. The point where the thickness of the material increases acts as a hinge or fulcrum so that the more distal portion of the finger is more easily flexed. The wedge may also take the shape of a tapered wedge, not a step down wedge, in which the thickness of the material is constantly decreasing from its thickest to thinnest point. The median phalangeal thickness of the tapered wedge should approximate the thickness of the preferred design.

The preferred design is one in which the thickness differential is that of a tapered stepped design, whereby, the taper occurs at the flex tubule. In the stepped design, it is possible to have a tapered form located at the step. The design can be of a solid film or material which may be of geometric shape or portion of a geometric shape, for example a solid ¼ round circle, or an arc. A stiffer material may be embedded into the thicker segment as the step down or as the filler in the geometric shape to increase the ability of the material to act as a fulcrum on itself in the flexion and extension motion.

The wedge design is the driver to provide maximum mechanical advantage and user functionality. Wedge thickness ratios are based on the films employed and are derive so as to provide maximum resistance to puncture, cuts, infusions of liquids, chemical, or biological agents. Thus ease of flexion of the finger with a stiff material is improved. Please note that the outer surface of the glove is smooth and that the variations in thickness occur along the inner surface.

An alternate design is to have a reverse wedge design on the dorsum of the glove which follows the mathematical sequence in which the finger tip area is the thickest and the wrist area is the thinnest, the reverse of the palmar wedge.

An alternate design of the medial and lateral surfaces of the fingers and hand may have the wedge design.

The combination of the wedge and flex point design both aid in the flexion mechanism.

The preferred method is that of hermetically sealing or air evacuation of the films. There is an advantage to applying a film which is resistant to reactive chemicals, if the chemical resistant film were flexible and soft, the film would may act to aid in the puncture resistance enhancement of the primary puncture resistant material. If a thin film of acrylic was the chemical resistant film and were to be applied to the puncture resistant film, the acrylic film is very soft and very flexible. When a metal instrument violates the film, this film would slow the speed of the object, as a result, greater puncture resistance.

More than one area of the glove may have on it adhered embossed or ingrained within its film non slip gripping patterns. The inside design of the glove may be altered so that a design may be imparted to its surface to facilitate hand insertion, the design may be of full thickness or partial thickness of one or more films of the glove. A film or coating can be applied to the inner and/or outer surface of the glove which will protect the operator's hand from reactive chemicals, the film may or may not be adhered to the nylon inner surface of the glove, if adhered, the adherence may be by any means including friction. A material may be applied to the exterior surface of the glove or a pattern may be embossed into the surface or shaped within the surface of the glove to increase the friction co-efficient of the glove to increase the gripping ability of the operator. The inside surface of the glove can have a design embossed full or partial thickness or a material applied to its surface to facilitate hand insertion.

Let's look at some interesting relationships which exist with the glove. The preferred design is based on a distinctive set of mathematical relationships. The accordion folds of the dorsum of the hand are three at the distal interphalangeal joint and the interphalangeal joint of the thumb, fives at the proximal interphalangeal joint and the metacarpophalangeal joint of the thumb, eight at the metacarpophalangeal joints of the fingers and the metacarpal trapezium joint of the thumb, and thirteen at the wrist. The palmar flex tubules are one, one, two (or one), and three Grey's Anatomy, describes three creases at the wrist. There is one straight accordion fold for the distal interphalangeal joints of the fingers and the interphalangeal joint of the thumb. One straight accordion fold for the proximal interphalangeal joints of the fingers and for the metacarpophalangeal joint of the thumb, two straight accordion folds for the metacarpophalangeal joints of the fingers and for the metacarpal trapezium joint of the thumb, and three for the wrist. There are three accordion fold for the web spaces, five for the medial surface of the palm and eight for the forearm. The diameter of the flex tubules are 1/16th", 1/16th", 2/16th", and 3/16th" respectively. The wedge shows a relationship of one thickness, two thickensses, three thicknesses, and five thicknesses. When this is done, there is a significant increase in the amount of sharps protective material and the slight angulation of about one degree is relatively imperceptible to the operator, but gives a mechanical advantage to the ability for one to flex the film. The preferred design geometric figure is the bell curve, it has three points on which it can move on itself or flex. The design contains one, two, or three means of providing body fluid and infectious disease particulate material from coming into contact with the operator's skin. The preferred method of constructing the glove is in the organized, effective mathematical sequence format. The following are Fibanacci numbers, 0,1,1,2,3,5,8,13. The Fibanacci number sequence is adding the first two numbers to derive the third. All preferred designs of the glove are Fibanacci numbers and Fibanacci number sequences The packaging of the gloves may be color coded as to the size of the glove along with printing the size on the package, this system may facilitate the user greater ease in locating the proper size. The size of the glove could be stamped on the glove itself in the proper color for its size if the materials to do this were non-toxic.

Alternate means of producing the glove's design can vary from the preferred in a manor in which any and/or all of the accordion folds, flex tubules, number of straps, and thickness of the material are altered.

The preferred glove can be manufacture in a number of methods, they include the use of melted or molten material, the use of the material in sheet form, and vacuum forming.

If the glove is to be produced via the melted format, the material is either poured or injected into a two piece mold of the palmar surface which has all design features incorporated into the mold. The melted material is either poured or injected into a second two piece mold. This mold contains all the design features of the dorsal, medial, and lateral surfaces of the glove. Each two piece mold set provides a positive and negative mold. The molten material is inserted between the positive and negative mold halves. Pressure is applied and the resultant is allowed to cool. The next step requires a full positive mold of the full hand, both formed halves of the glove are placed on the mold, the parts are aligned, fused, and the excess material removed.

If the manufacturing of the glove is to be done with a sheet of the material, six cutting dies, a two piece mold of the palmar surface of the glove, a two piece mold of the medial, lateral, and dorsal surfaces of the glove, and one positive mold of the entire hand.

A cutting die cuts the sheet of material which is 0.007" in thickness in the shape of the palmar surface of the glove. A second die cuts a sheet of the material 0.007" in thickness, in the shape of the palmar surface of the glove which in this case the cut ends at the distal interphalangeal joint and the interphalangeal joint of the thumb. A third die cuts a sheet of material 0.007" in thickness in the shape of the palmar surface of the glove which in this case, ends at the proximal interphalangeal joint of the fingers and the metacarpophalangeal joint of the thumb. A fourth die cuts a sheet of the material 0.014" in thickness in the shape of the palmar surface of the glove which in this case, ends at the metacarpophalangeal joints of the fingers and the thenar eminence of the palm. A fifth die cuts the material 0.020" in thickness in the shape of the forearm which in this case, ends at the wrist. A sixth die cuts the material 0.028" in thickness in the shape of the forearm which in this case ends at the wrist. The films are aligned in the proper thickness sequence on the negative mold of the palmar surface of the glove which contains the designs. Heat and pressure shaping are gradually applied to the mold, the resultant is a solid film of varying thickness embossed with the preferred design. During the forming process, the heat and pressure must be applied gradually as well as the cooling process to avoid distortion. In a negative mold of the dorsal, medial and lateral surfaces on which contain the preferred designs of each surface, the films are placed. The same process for the palmar surface is utilized. The result is in a portion of the glove which is a solid film of varied thickness. An alternative means of producing the glove from the solid sheet of material is to substitute a bonding agent instead of heating the material. Again, the bonding process, embossing process, and cooling process should be done gradually to avoid distortion of the design. Both haves are placed on a positive of a hand, aligned, fused and trimmed.

The strap and locking seal could be adhered to the glove following with either process with either glue, or welding. The soft pliable conforming inner seal of the strap would then be applied to the inner surface of the forearm, and now the preferred glove is complete.

I claim:

1. A surgical or examination glove comprising connected palm, fingers, thumb, wrist and forearm portions having palmar, medial, lateral and dorsal surfaces comprising a layer of film impervious to body fluids and being cut and puncture resistant, the glove having palmar distal phalangeal finger segments with a thickness less than a thickness of the rest of the palmar surface of the glove, palmar middle phalangeal finger segments of the glove having a thickness more than the thickness of the palmar distal phalangeal finger segments and equal to a thickness of a palmar distal phalangeal thumb segment, palmar proximal phalangeal finger segments of the glove having a thickness similar to a thickness of a palmar proximal phalangeal thumb segment, a thenar portion of the palm and a palmar segment of the palm having a thickness greater than a thickness of the palmar proximal phalangeal finger segments, and a forearm segment having a thickness greater than a thickness of the rest of the glove, the most distal segments of the palmar surface of the fingers being thinner than the palmar middle segments and having a thickness not greater than thicknesses of the medial, lateral and dorsal surfaces of the glove, and the palmar surface having an increasing thickness in a direction extending from the distal phalangeal segments to the forearm.

2. The glove of claim 1, further comprising a palmar side of each of the portions and a dorsum of each of the portions, wherein the palmar side has parallel spaced single grooves to allow and facilitate flexion, and wherein the dorsum has plural spaced accordion folds for allowing expansion of the dorsum of the glove longitudinally between the wrist portion and the distal finger portions and for providing concave arcing of the front of the finger, thumb, palm, and wrist portions for providing adequate tactile sensation and flexibility at the distal segments, wherein each segment is adhered to an adjacent segment, and the wrist is adhered to the forearm portion.

3. The glove of claim 1, wherein the glove comprises moldable materials and is adaptable to individual users.

4. The glove of claim 1, wherein varied glove thicknesses of the glove portions provide for the puncture resistance, and the glove having a flex point design allowing for greater thickness of the cut and puncture resistant film in portions of the glove not needed for tactile sensation.

5. The glove of claim 1, further comprising molded flex areas having a surface coating for providing increased gripping ability due to friction without compromising tactile sensitivity.

6. The glove of claim 1, further comprising molded flex areas for providing improved flexibility and for allowing molding of the glove with a solid film impervious to body fluid and having an improved out and puncture resistance.

7. The glove of claim 1, wherein the film is a single thickness fluid resistant film having a flex point, and wherein the film has a pre-determined varied thickness corresponding to the varied thicknesses of the glove portions for forming the glove.

8. The glove of claim 1, further comprising the palmar surface of the glove being adhered to a latex glove, the palmar surface being of a single layer solid film resistant to cuts and punctures.

9. The glove of claim 1, further comprising a flexible material attached to an inner surface of the glove forming a strap for tightening the glove and providing a tight seal to prevent fluids from entering within the glove when in use.

10. The glove of claim 9, further comprising an additional strap provided on the forearm portion for attaching to a gown of a user and sealing an area around the strap for preventing extraneous matter from entering the glove when in use, said sealing allowing for removal of the user's gown along with the gloves and preventing contact with any material being handled when the glove is in use.

11. The glove of claim 1, wherein the glove is a surgical glove having variable thicknesses and flexion.

12. The glove of claim 1, wherein the glove is a multi-purpose glove having variable thicknesses and flexion.

* * * * *